(12) United States Patent
Krebs et al.

(10) Patent No.: US 6,610,864 B2
(45) Date of Patent: Aug. 26, 2003

(54) PROCESS FOR THE EPOXIDATION OF CIS DOUBLE BONDS

(75) Inventors: Bernt Krebs, Muenster (DE);
Elisabeth Droste, Goslar (DE);
Markus Piepenbrink, Muenster (DE);
Guido Vollmer, Guetersloh (DE);
Georg Oenbrink, Duelmen (DE);
Thomas Schiffer, Haltern (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/985,478

(22) Filed: Nov. 5, 2001

(65) Prior Publication Data

US 2002/0091275 A1 Jul. 11, 2002

(30) Foreign Application Priority Data

Nov. 8, 2000 (DE) ......................................... 100 55 173

(51) Int. Cl.$^7$ ............................................. C07D 301/12
(52) U.S. Cl. ....................................... 549/531; 549/533
(58) Field of Search ................................. 549/531, 533

(56) References Cited

U.S. PATENT DOCUMENTS

| | | | |
|---|---|---|---|
| 3,806,467 A | 4/1974 | Watanabe et al. |
| 4,562,276 A | 12/1985 | Venturello et al. |
| 4,864,041 A | 9/1989 | Hill |
| 5,430,161 A | 7/1995 | Brown et al. |
| 5,684,071 A | 11/1997 | Mogami et al. |

FOREIGN PATENT DOCUMENTS

| | | | |
|---|---|---|---|
| EP | 0 549 077 | | 6/1993 |
| EP | 0 950 659 A2 | | 10/1999 |
| GB | 2 055 821 | | 3/1981 |
| WO | 98/54165 | * | 12/1998 |

OTHER PUBLICATIONS

M. Bösing, et al., J. Am. Chem. Soc., vol. 120, No. 29, pp. 7252–7259, XP–002193323, "Highly Efficient Catalysts in Directed Oxygen–Transfer Processes: Synthesis, Structures of Novel Manganese–Containing Heteropolyanions, and Applications in Regioselective Epoxidation of Dienes with Hydrogen Peroxide", 1998.

J–Y. Piquemal, et al., Comptes Rendus de'l Academie des Sciences, vol. 319, No. 12, pp. 1481–1487, XP–000494280, "Syntheses, Structures et Reactivite De L'Anion ($\mu$–Hydrogenoarsenato)Bis($\mu$–Peroxo)Bis(Oxoperoxotungstate) (2–) et de Son Analogue Avec le Ligand Methylarsenate Cristallises Avec le Cation Tetrabutylammonium", Dec. 15, 1994.

L. Salles, et al., Inorg. Chem., vol. 33, No. 5, pp. 871–878, XP–002078716, "$^{31}$P and $^{183}$W NMR Spectroscopic Evidence for Novel Peroxo Specials in the "H$^3$[PW$_{12}$O$_{40}$].yH$_2$O/H$_2$O$_2$"System. Synthesis and X–Ray Structure of Tetrabutylammonium ($\mu$–Hydrogen Phosphato ) Bis($\mu$–Peroxo) Bis(Oxoperoxotungstate) (2–): A Catalyst of Olefin Epoxidation in a Biphase Medium, Mar. 2, 1994.

Forbes, et al., "Effect of Localized Unsaturation on the Scalar Exchange Coupling in Flexible Biradicals", The Journal of Physical Chemistry (1993), vol. 97, No. 13, pp. 3390–3395.

Boesing, et al., "Low–temperature bleaching with manganese–containing heteropolytungstates", Applied Catalysis A: General 184 (1999), pp. 273–278.

Loose, et al., "Heteropolymetalate Clusters of the Subvalent Main Group Elements Bi$^{III}$ and Sb$^{III}$", Inorganic Chemistry (1999), vol. 38, No. 11, pp. 2688–2694.

* cited by examiner

*Primary Examiner*—Taofiq Solola
(74) *Attorney, Agent, or Firm*—Oblon, Spivak, McClelland, Maier & Neustadt, P.C.

(57) ABSTRACT

The selective epoxidation of cis double bonds of macrocyclic aliphatic hydrocarbons having 8 to 20 ring carbon atoms occurs by a catalytic process. The macrocyclic aliphatic hydrocarbons may optionally contain one or more side chains and in which at least one further trans double bond is simultaneously present. The used catalyst system consists of a cationic phase-transfer catalyst and an anionic polyoxometallate which is a polytungstate or a polymolybdate. Additionally, it comprises one or more elements selected from germanium, tin, lead, arsenic, antimony, bismuth, selenium, tellurium and polonium, and optionally one or more transition metals from group 4 to 12 of the Periodic Table.

18 Claims, 1 Drawing Sheet

PROCESS FOR THE EPOXIDATION OF CIS DOUBLE BONDS

BACKGROUND OF THE INVENTION

1. Field of the Invention

The present invention relates to a catalytic process for the selective epoxidation of cis double bonds in macrocyclic aliphatic hydrocarbons.

2. Discussion of the Background

Macrocyclic olefins are important building blocks in the synthesis of numerous specialty chemicals. An important representative of such cyclic hydrocarbons is cis,trans,trans-1,5,9-cyclododecatriene, which is formed on an industrial scale by the cyclotrimerization of 1,3-butadiene, preferably on a titanium catalyst, and is used as the precursor for cyclododecanone, dodecanedioc acid and laurolactam/nylon 12.

Numerous processes for the epoxidation of macrocyclic olefins are known. Organic peracids, such as performic acid, peracetic acid or perpropionic acid, can be employed. EP-A-0 033 763 (Degussa AG) describes the reaction of cyclododecatriene (CDT) with performic acid, which is formed in situ from hydrogen peroxide and formic acid. EP-A-0 032 990 (Henkel KGaA, Degussa AG) describes the reaction of derivatives of cyclododecatriene with performic acid. In the case of acid-sensitive olefins, problems arise from side reactions or subsequent reactions which the epoxides can undergo under the acidic reaction conditions. The acid-catalyzed addition of water onto the epoxide results in a vicinal diol; isomerization at the double bonds also occurs.

EP-A 0 055 387 (Peroxid-Chemie) therefore recommends neutralizing the carboxylic acids remaining before the epoxidation as an improvement after the synthesis of the peracid. Besides peracetic acid, perpropionic acid and perbutyric acid are also claimed as oxidants. This process has the disadvantage of large amounts of salt that are formed during the neutralization. The oxidation with other peracids, such as meta-chloroperbenzoic acid (M. D. E. Forbes, J. Phys. Chem. 97 (1993) 3390–3395) is, as already stated in EP-A-0 055 387, uneconomical on an industrial scale.

The epoxidation with a peracid proceeds nonselectively with respect to attack on the cis double bond. W. Stumpf and K. Rombusch (Ann. Chem. 687 (1965) 136–149) were able to show in the systematic study of the reaction of cis,trans,trans-1,5,9-cyclododecatriene with performic acid that one of the two trans double bonds is attacked to the extent of 92% and the cis double bond is attacked to the extent of only 7%. This gives a trans:cis reactivity of 6.5:1. As a consequence, the two trans double bonds of cis,trans,trans-1,5,9-cyclododecatriene are preferentially attacked in the presence of an excess of oxidant, and considerable amounts of diepoxide are formed.

Besides the undesired trans selectivity, it should be noted that on use of organic peracids, large amounts of organic acids are formed and have to be separated from the reaction mixture and worked up. In addition, the use of organic peracids on an industrial scale requires considerable safety efforts, which is also pointed out in EP-A-0 032 990 and EP-A-0 033 763. To date, industrial processes using organic peracids for the epoxidation of cyclododecatriene have not become established.

The difficulties in working up large amounts of organic carboxylic acids can be circumvented if the peracid is replaced by other oxygen sources in combination with catalytic amounts of transition-metal salt as an oxidant.

The transition-metal catalysts used are frequently based on compounds from sub-group 6 of the Periodic Table, in particular on tungsten and molybdenum. These transition metals are preferably employed in the form of their polyacids or heteropolyacids or as polyoxometallate anions.

Monoolefins can easily be epoxidized at high conversion rates and yields using such catalysts by means of a large excess of oxidant. Typical monoolefins on which catalyst systems of this type are tested are cyclohexene and cyclooctene. The oxidants used, besides hydrogen peroxide, are also atmospheric oxygen (WO 98/54165, Yissum Research Institute, DD 212960, Akademie der Wissenschaften) and iodosylbenzene or the pentafluorinated derivative (U.S. Pat. No. 4,864,041, Emory University).

In the liquid phase, the reaction can be carried out in one phase or two phases. If two liquid phases are present and the transition metal is used as a homogeneous catalyst, its action is improved by phase-transfer catalysts, typically quaternary ammonium, pyridinium or phosphonium salts.

Processes in which the catalyst is adsorbed onto an inorganic or organic support material are described, for example, in WO 93/00338 (Solvay Interox) and U.S. Pat. No. 5,684,071.

The synthesis is significantly more difficult if, as in the case of cyclododecatriene, only one of a plurality of double bonds in the molecule is to be epoxidized selectively. In the current state of the art, hydrogen peroxide is employed in a large sub-stoichiometric amount, and the reaction must be terminated after relatively low conversions (typically <25%), so that the selectivity of the reaction does not drop below 90%. Based on these teachings, Ube Industries in EP-A-0 950 659 have recently described an industrial process for the synthesis of CDT monoepoxide in which a multistage reactor cascade is operated at from 20° C. to 120° C.

The catalyst claimed by Ube is the combination of a quaternary ammonium salt or pyridinium salt with a tungsten-containing acid or salts thereof, dodecatungstate, tungsten-containing heteropolyacids or salts thereof. In the examples given, the reaction with sodium tungstate dihydrate ($Na_2WO_4.2\ H_2O$) and tungstophosphoric acid ($H_3PO_4.12WO_3.x\ H_2O$) described specifically. The latter has the disadvantage that acid-sensitive epoxides undergo subsequent reactions. In addition, the aqueous solution has a highly corrosive action.

In the examples, cyclododecatriene and hydrogen peroxide are employed in the ratio 4:1. At the end of the reactor cascade, from 21.5 to 22.1 mol % of CDT have been reacted, giving a selectivity of monoepoxide of from 91.2 to 94.2 mol %.

In comparison (EP-A-0 950 659, Example 5), Ube quotes the reaction with tungstophosphoric acid on a laboratory scale at a $CDT:H_2O_2$ ratio of 5:1, in which 18.2 mol % of CDT are converted into the monoepoxide with a selectivity of 95.0 mol %.

The patent applicant mentions as an advantage of his own process the comparatively high conversion rate and yield. Although the latter, at about 22 mol %, is better than in the comparative example indicated, about 78 mol % of unreacted cyclododecatriene must nevertheless still be separated off during work-up and circulated in this process.

SUMMARY OF THE INVENTION

Therefore, it is an object of the present invention to develop a process which is distinguished by the fact that a cis double bond in a macrocyclic olefin is epoxidized as selectively as possible in the presence of at least one further trans double bond with a conversion of greater than 25%.

A further object of the present invention is to find a neutral catalyst system to enable the process also to be employed in the synthesis of acid-labile epoxides.

Surprisingly, it has now been found that both objects are achieved by the use of specific polyoxometallates of molybdenum and of tungsten.

The above and other objects of the present invention have been achieved by a process for the preparation of a macrocyclic monoepoxide containing at least one double bond, comprising:

reacting a macrocyclic aliphatic hydrocarbon containing at least one cis double bond and at least one trans double bond with hydrogen peroxide in two liquid phases in the presence of a homogeneous catalyst system;

wherein said homogeneous catalyst system consists of an oxidation catalyst and a phase-transfer catalyst; and wherein said oxidation catalyst consists of a) a polyoxometallate of tungsten or molybdenum and b) at least one element from group 14 to 16 of the Periodic Table.

DETAILED DESCRIPTION OF THE INVENTION

Figure 1:
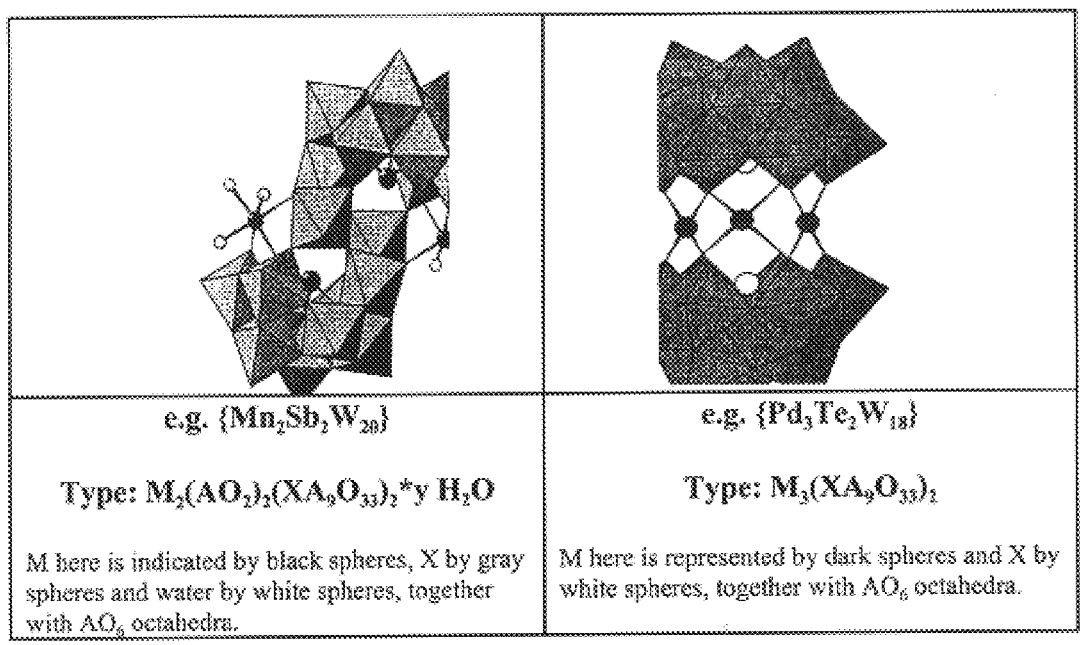
FIG. 1 shows the spacial structures of $M_2(AO_2)_2(XA_9O_{33})_9 \cdot 6H_2O$ and $M_3(MX_9O_{33})_2$.

The present invention relates to a process for the preparation of a macrocyclic monoepoxide which also contains at least one double bond. The starting material is a macrocyclic aliphatic hydrocarbon which contains at least one cis double bond in the presence of at least one further trans double bond. The macrocyclic aliphatic hydrocarbon is reacted with hydrogen peroxide in the presence of a catalyst system. The reaction mixture comprises two liquid phases. A homogeneous catalyst system consisting of an oxidation catalyst and a phase-transfer catalyst is used. The oxidation catalyst consists of a) a polyoxometallate of tungsten or of molybdenum and of b) at least one further element from groups 14 to 16 of the Periodic Table. This element is selected from the group which is formed by the elements germanium, tin, lead, arsenic, antimony, bismuth, selenium, tellurium and polonium. The oxidation catalyst optionally comprises one or more transition metals from groups 4 to 12, and the phase-transfer catalyst used is a quaternary ammonium ion, pyridinium ion or phosphonium ion as counterion.

Typical representatives of the transition metals from groups 4 to 12 are titanium, vanadium, chromium, manganese, iron, cobalt, nickel, palladium, copper and zinc.

Representatives of the polyoxometallate anions according to the invention preferably have structures of the formulae

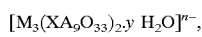

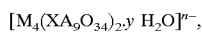

or

where the letters A, M and X represent the following elements:

M=Ti, V, Cr, Mn, Fe, Co, Ni, Pd, Cu, Zn, Sn or As

A=Mo or W

X=Ge, Sn, Pb, As, Sb, Bi, Se, Te or Po, and n is a number from 6 to 12, y is a number from 0 to 6, and z is a number from 0 to 3.

As non-limiting examples of polyoxometallate anions of this type, FIG. 1 shows the spatial structures of $M_2(AO_2)_2(XA_9O_{33})_2 \cdot 6H_2O$ and $M_3(MX_9O_{33})_2$, as determined by X-ray structural analysis.

The polyoxometallate anions are usually mentioned in abbreviated notation, in which the oxygen atoms, water bonded to the heteroatoms, and the charge of the polyoxometallate anions are omitted. The curly brackets indicate that this is not a complete empirical formula, but instead the ratio of the elements M, X and A. Thus, for example, the empirical formula $[Mn_2(WO_2)_2(SbW_9O_{33})_2 \cdot 6\ H_2O]^{10-}$ is represented by the abbreviated notation $\{Mn_2Sb_2W_{20}\}$.

The polyoxometallates are initially prepared in the form of their alkali metal or alkaline earth metal salts, preferably as sodium or potassium salts, or their mixed salts. Corresponding syntheses are described, for example, in the German Patent Application DE 195 30 787 A1, Inorg. Chem. 38 (1999), 2688–2694 or Applied Catalysis A: General 184 (1999), 273–278, and the references cited therein.

For the active catalyst species, these cations are replaced by a cationic phase-transfer catalyst. The active catalyst is readily soluble both in the aqueous phase and in the organic phase and can be stored dissolved in the organic phase for up to 10 days at 4° C.

Preferred representatives of the cations used are those of quaternary ammonium salts with conventional anions of the form $R_1R_2R_3R_4N^+$, where $R_1$ to $R_4$ are each, independently of one another, hydrogen or an alkyl group having 1 to 20 carbon atoms, which may also contain branches. Particularly preferred examples of such cations are methyltrioctylammonium, cetyltrimethylammonium and tetrabutylammonium. In addition, other phase-transfer cations, such as those of N-alkylated pyridinium salts or quaternary phosphonium salts, are preferred.

The reaction is carried out in the liquid phase and can be carried out either batchwise, for example, in a stirred-tank reactor, or continuously, for example in a cascade of stirred-tank reactors. The system is operated in two phases, the first phase consisting of an aqueous solution of hydrogen peroxide and the second phase consisting of an inert, organic, water-immiscible solvent. Non-limiting examples of organic solvents are both halogen-containing compounds, such as, for example, dichloromethane, 1,2-dichloroethane, chloroform and tetrachloromethane, and halogen-free compounds, such as, for example, benzene, toluene, xylenes, or alkanes and cycloalkanes having, in particular, 5 to 12 carbon atoms, such as, for example, n-hexane.

The reaction is usually carried out at from 0° C. to 120° C., preferably at from 5° C. to 80° C. The temperature includes all values and subvalues therebetween, especially including 10, 20, 30, 40, 50, 60, 70, 80, 90, 100 and 110° C. The reaction is generally carried out at atmospheric pressure; at higher reaction temperatures, an increased pressure may arise due to the vapor pressures of the solvents used.

The oxidant used is hydrogen peroxide. Solutions having a content of from 0.1 to 85% by volume are preferred. The content of hydrogen peroxide includes all values and subvalues therebetween, especially including 10, 20, 30, 40, 50, 60, 70 and 80% by volume. Particular preference is given to 30 to 70% by volume solutions. Any solvent that dissolves hydrogen peroxide can be used. The preferred solvent is water.

The conversion of the macrocyclic aliphatic hydrocarbon and selectivity for monoepoxide are followed by gas chromatography. The peroxide content can be determined by redox titration of the aqueous phase.

The reaction is terminated by separation of the phases. In the batch procedure, this is carried out in the reactor by switching off the stirrer and separating the phases. In the continuous procedure, the phase separation is usually carried out in a downstream separation tank.

The conversion of the macrocyclic aliphatic hydrocarbon is preferably at least 25%. The selectivity for monoepoxide is preferably at least 90%, more preferably at least 95% and most preferably at least 99%. In particular, the proportion of trans,trans-5,9-cyclododecadiene 1-epoxide compared to cis,trans-5,9-cyclododecadiene 1-epoxide in the product mixture is at least 35 mol %, more preferably at least 55%, most preferably at least 65%.

Having generally described this invention, a further understanding can be obtained by reference to certain specific examples which are provided herein for purposes of illustration only, and are not intended to be limiting unless otherwise specified.

EXAMPLES

For the catalyst classification (Examples 1–12 and Comparative Examples 13–14), the following standard batch was selected, in which the short formulae indicated correspond to the following polyoxometallate anions employed:

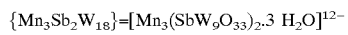

$\{Mn_3Sb_2W_{18}\}=[Mn_3(SbW_9O_{33})_2\cdot 3\ H_2O]^{12-}$

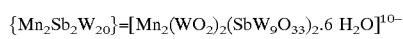

$\{Mn_2Sb_2W_{20}\}=[Mn_2(WO_2)_2(SbW_9O_{33})_2\cdot 6\ H_2O]^{10-}$

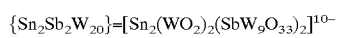

$\{Sn_2Sb_2W_{20}\}=[Sn_2(WO_2)_2(SbW_9O_{33})_2]^{10-}$

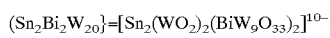

$\{Sn_2Bi_2W_{20}\}=[Sn_2(WO_2)_2(BiW_9O_{33})_2]^{10-}$

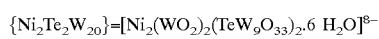

$\{Ni_2Te_2W_{20}\}=[Ni_2(WO_2)_2(TeW_9O_{33})_2\cdot 6\ H_2O]^{8-}$

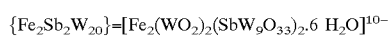

$\{Fe_2Sb_2W_{20}\}=[Fe_2(WO_2)_2(SbW_9O_{33})_2\cdot 6\ H_2O]^{10-}$

$\{Mn_2Bi_2W_{20}\}=[Mn_2(WO_2)_2(BiW_9O_{33})_2\cdot 6\ H_2O]^{10-}$

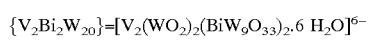

$\{V_2Bi_2W_{20}\}=[V_2(WO_2)_2(BiW_9O_{33})_2\cdot 6\ H_2O]^{6-}$

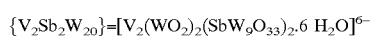

$\{V_2Sb_2W_{20}\}=[V_2(WO_2)_2(SbW_9O_{33})_2\cdot 6\ H_2O]^{6-}$

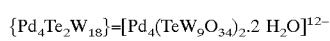

$\{Pd_4Te_2W_{18}\}=[Pd_4(TeW_9O_{34})_2\cdot 2\ H_2O]^{12-}$

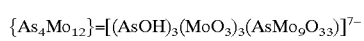

$\{As_4Mo_{12}\}=[(AsOH)_3(MoO_3)_3(AsMo_9O_{33})]^{7-}$

$\{MnAs_4Mo_{12}\}=[(AsOH)_{3-z}Mn_z(MoO_3)_3(AsMo_9O_{33})]^{7-}$

Preparation of the Catalyst Solutions:

In order to prepare the catalyst solutions, 0.064 mmol of the polyoxometallate in the form of the alkali metal or alkaline earth metal derivative was refluxed with 258 mg (0.64 mmol) of methyltrioctylammonium chloride in 20 ml of a 1:1 mixture of water/1,2-dichloroethane until the solids were dissolved and the aqueous phase was completely decolorized (about 30 minutes). The colored, organic phase was separated off. The organic phase was storable for a few days at +4° C.

Epoxidation:

3.25 g (20.0 mmol) of cis,trans,trans-1,5,9-cyclododecatriene were dissolved in 5 ml of 1,2-dichloroethane, and 3.125 ml of catalyst solution (corresponding to 0.02 mmol of the respective polyoxometallate) were added. 2.0 equivalents (40.0 mmol) of hydrogen peroxide, employed as a 30% strength aqueous solution, were added, and the mixture was stirred at 800 rpm at atmospheric pressure and 25° C. A substrate/$H_2O_2$/catalyst ratio of 1000:2000:1 thus arose. The course of the reaction was monitored by regular GC/MS measurements.

The results are summarized in the following tables.

EXAMPLE 1

$\{Mn_3Sb_2W_{18}\}$

| Time [h] | Mono-epoxide [%] | Diepoxide [%] | CDT conversion [%] | Selectivity [%] | TOF [mmol$_{CDT}$/(mmol$_{cat}$ · h)] |
|---|---|---|---|---|---|
| 1 | 24.3 | <0.1 | 24.3 | >99 | 243 |
| 2.5 | 42.0 | 4.2 | 46.2 | 90.9 | 185 |
| 4 | 51.9 | 7.2 | 60.1 | 86.4 | 150 |
| 6 | 56.1 | 15.4 | 71.5 | 78.5 | 119 |
| 30 | 38.3 | 58.9 | 97.2 | 39.4 | 41 |

EXAMPLE 2

$\{Mn_2Sb_2W_{20}\}$

| Time [h] | Mono-epoxide [%] | Diepoxide [%] | CDT conversion [%] | Selectivity [%] | TOF [mmol$_{CDT}$/(mmol$_{cat}$ · h)] |
|---|---|---|---|---|---|
| 1 | 12.1 | <0.1 | 12.1 | >99 | 121 |
| 4 | 38.9 | <0.1 | 38.9 | >99 | 97 |
| 6 | 52.9 | 6.9 | 59.8 | 88.5 | 99 |
| 24 | 55.4 | 36.1 | 91.5 | 60.5 | 38 |

EXAMPLE 3

$\{Sn_2Sb_2W_{20}\}$

| Time [h] | Mono-epoxide [%] | Diepoxide [%] | CDT conversion [%] | Selectivity [%] | TOF [mmol$_{CDT}$/(mmol$_{cat}$ · h)] |
|---|---|---|---|---|---|
| 1 | 12.4 | <0.1 | 12.4 | >99 | 124 |
| 4 | 51.3 | <0.1 | 51.3 | >99 | 128 |
| 6 | 66.2 | 1.5 | 67.7 | 97.8 | 113 |
| 24 | 48.7 | 45.4 | 94.1 | 51.8 | 39 |

EXAMPLE 4

$\{Sn_2Bi_2W_{20}\}$

| Time [h] | Mono-epoxide [%] | Diepoxide [%] | CDT conversion [%] | Selectivity [%] | TOF [mmol$_{CDT}$/(mmol$_{cat}$ · h)] |
|---|---|---|---|---|---|
| 1 | 9.0 | <0.1 | 9.0 | >99 | 90 |
| 4 | 57.4 | 0.8 | 58.2 | 98.2 | 146 |
| 6 | 57.9 | 11.1 | 69.0 | 83.9 | 115 |
| 24 | 53.8 | 38.8 | 92.6 | 58.1 | 39 |

EXAMPLE 5

| | | | {Ni$_2$Te$_2$W$_{20}$} | | |
|---|---|---|---|---|---|
| Time [h] | Monoepoxide [%] | Diepoxide [%] | CDT conversion [%] | Selectivity [%] | TOF [mmol$_{CDT}$/(mmol$_{cat}$ · h)] |
| 1 | 16.0 | 0.3 | 16.3 | 98.2 | 163 |
| 2 | 36.8 | 7.3 | 44.1 | 83.4 | 221 |
| 4 | 53.4 | 10.7 | 64.1 | 83.3 | 160 |
| 6 | 59.9 | 18.3 | 78.2 | 76.6 | 130 |
| 24 | 45.1 | 52.1 | 97.2 | 46.4 | 41 |

EXAMPLE 6

| | | | {Fe$_2$Sb$_2$W$_{20}$} | | |
|---|---|---|---|---|---|
| Time [h] | Mono-epoxide [%] | Diepoxide [%] | CDT conversion [%] | Selectivity [%] | TOF [mmol$_{CDT}$/(mmol$_{cat}$ · h)] |
| 1 | 4.4 | <0.1 | 4.4 | >99 | 44 |
| 2 | 10.2 | <0.1 | 10.2 | >99 | 51 |
| 4 | 19.0 | <0.1 | 19.0 | >99 | 48 |
| 6 | 24.2 | 0.1 | 24.3 | >99 | 41 |
| 24 | 28.4 | 0.2 | 28.6 | >99 | 12 |

EXAMPLE 7

| | | | {Mn$_2$Bi$_2$W$_{20}$} | | |
|---|---|---|---|---|---|
| Time [h] | Mono-epoxide [%] | Diepoxide [%] | CDT conversion [%] | Selectivity [%] | TOF [mmol$_{CDT}$/(mmol$_{cat}$ · h)] |
| 1 | 12.1 | <0.1 | 12.1 | >99 | 121 |
| 2 | 18.5 | <0.1 | 18.5 | >99 | 93 |
| 4 | 38.9 | 0.1 | 39.0 | >99 | 97 |
| 6 | 52.9 | 6.9 | 59.8 | 88.5 | 99 |
| 24 | 55.4 | 36.0 | 91.4 | 60.6 | 38 |

EXAMPLE 8

| | | | {V$_2$Bi$_2$W$_{20}$} | | |
|---|---|---|---|---|---|
| Time [h] | Mono-epoxide [%] | Diepoxide [%] | CDT conversion [%] | Selectivity [%] | TOF [mmol$_{CDT}$/(mmol$_{cat}$ · h)] |
| 1 | 12.6 | <0.1 | 12.6 | >99 | 126 |
| 2 | 28.0 | <0.1 | 28.0 | >99 | 140 |
| 4 | 43.2 | 0.2 | 43.4 | >99 | 109 |
| 6 | 51.1 | 7.6 | 58.7 | 87.1 | 98 |
| 24 | 54.9 | 34.7 | 91.4 | 60.0 | 38 |

EXAMPLE 9

| | | | {V$_2$Sb$_2$W$_{20}$} | | |
|---|---|---|---|---|---|
| Time [h] | Mono-epoxide [%] | Diepoxide [%] | CDT conversion [%] | Selectivity [%] | TOF [mmol$_{CDT}$/(mmol$_{cat}$ · h)] |
| 1 | 10.7 | <0.1 | 10.7 | >99 | 107 |
| 2 | 20.1 | 0.1 | 20.2 | >99 | 101 |
| 4 | 41.2 | 4.2 | 45.4 | 90.7 | 109 |
| 6 | 52.9 | 8.6 | 61.5 | 86.0 | 103 |
| 24 | 57.8 | 28.1 | 85.9 | 67.2 | 36 |

EXAMPLE 10

| | | | {Pd$_4$Te$_2$W$_{18}$} | | |
|---|---|---|---|---|---|
| Time [h] | Mono-epoxide [%] | Diepoxide [%] | CDT conversion [%] | Selectivity [%] | TOF [mmol$_{CDT}$/(mmol$_{cat}$ · h)] |
| 1 | 13.4 | <0.1 | 13.4 | >99 | 134 |
| 2 | 24.9 | <0.1 | 24.9 | >99 | 125 |
| 4 | 41.3 | 0.2 | 41.5 | >99 | 104 |
| 6 | 50.3 | 6.7 | 57.0 | 88.2 | 95 |
| 24 | 55.2 | 22.9 | 78.1 | 70.7 | 33 |

EXAMPLE 11

| | | | {As$_4$Mo$_{12}$} | | |
|---|---|---|---|---|---|
| Time [h] | Mono-epoxide [%] | Diepoxide [%] | CDT conversion [%] | Selectivity [%] | TOF [mmol$_{CDT}$/(mmol$_{cat}$ · h)] |
| 1 | 17.0 | <0.1 | 17.0 | >99 | 170 |
| 2 | 22.0 | <0.1 | 22.0 | >99 | 110 |
| 4 | 43.5 | 0.4 | 43.9 | 99.0 | 110 |
| 6 | 55.1 | 9.7 | 64.8 | 85.0 | 108 |
| 24 | 63.9 | 24.9 | 88.8 | 71.9 | 37 |

EXAMPLE 12

MnAs$_4$Mo$_{12}$

| Time [h] | Monoepoxide [%] | Diepoxide [%] | CDT conversion [%] | Selectivity [%] | TOF [mmol$_{CDT}$/(mmol$_{cat}$ · h)] |
|---|---|---|---|---|---|
| 1 | 7.0 | <0.1 | 7.0 | >99 | 70 |
| 2 | 10.1 | <0.1 | 10.1 | >99 | 50 |
| 4 | 18.1 | 0.1 | 18.2 | >99 | 46 |
| 6 | 26.3 | 0.2 | 26.5 | >99 | 44 |
| 24 | 54.0 | 7.9 | 63.9 | 84.5 | 27 |

Examples 13–16 show comparative examples with catalyst types which are not according to the invention. Examples 13 and 14 contain polyoxometallates without an element from main group 14–16 selected from germanium, tin, lead, arsenic, antimony, bismuth, selenium, tellurium and polonium. In Examples 15 and 16, the polyoxometallate anions were replaced by a solution of sodium tungstate dihydrate or tungstophosphoric acid (in each case 0.02 mmol as an aqueous solution with methyltrioctylammonium chloride as phase-transfer catalyst) in accordance with EP-A-0 950 659.

COMPARATIVE EXAMPLE 13

{Co$_4$W$_{19}$}

| Time [h] | Monoepoxide [%] | Diepoxide [%] | CDT conversion [%] | Selectivity [%] | TOF [mmol$_{CDT}$/(mmol$_{cat}$ · h)] |
|---|---|---|---|---|---|
| 1 | <0.1 | 0.0 | <0.1 | — | 0 |
| 4 | 1.5 | <0.1 | 1.5 | >99 | 4 |
| 24 | 10.6 | 0.1 | 10.7 | 99.0 | 4 |

COMPARATIVE EXAMPLE 14

{Fe$_6$W$_{18}$}

| Time [h] | Monoepoxide [%] | Diepoxide [%] | CDT conversion [%] | Selectivity [%] | TOF [mmol$_{CDT}$/(mmol$_{cat}$ · h)] |
|---|---|---|---|---|---|
| 24 | <0.1 | 0.0 | <0.1 | — | 0 |
| 75 | 0.6 | <0.1 | 0.6 | >99 | <1 |

COMPARATIVE EXAMPLE 15

Na$_2$WO$_4$·2 H$_2$O

| Time [h] | Monoepoxide [%] | Diepoxide [%] | CDT conversion [%] | Selectivity [%] | TOF [mmol$_{CDT}$/(mmol$_{cat}$ · h)] |
|---|---|---|---|---|---|
| 24 | 0.0 | 0.0 | 0.0 | — | — |
| 75 | <0.1 | 0.0 | <0.1 | — | — |

COMPARATIVE EXAMPLE 16

H$_7$[PW$_{12}$O$_{42}$]

| Time [h] | Monoepoxide [%] | Diepoxide [%] | CDT conversion [%] | Selectivity [%] | TOF [mmol$_{CDT}$/(mmol$_{cat}$ · h)] |
|---|---|---|---|---|---|
| 1 | 13.1 | <0.1 | 13.1 | >99 | 131 |
| 2 | 22.4 | 0.3 | 22.7 | 98.6 | 114 |

-continued

| | $H_4[PW_{12}O_{40}]$ | | | | |
|---|---|---|---|---|---|
| Time [h] | Monoepoxide [%] | Diepoxide [%] | CDT conversion [%] | Selectivity [%] | TOF [mmol$_{CDT}$/(mmol$_{cat}$ · h)] |
| 6.5 | 60.4 | 14.4 | 74.8 | 80.7 | 115 |
| 24* | 22.1 | 76.7 | 98.8 | 22.3 | 41 |

*Due to acid-catalyzed subsequent reactions, by-products, for example cyclododecadiene-1,2-diol, formed in Example 10 after a few hours due to addition of water onto the epoxide.
TOF = turn over frequency.

EXAMPLE 17

52 g (0.32 mol) of cis,trans,trans-cyclododecatriene were dissolved in 400 ml of dichloromethane in a 1 l reactor with heating jacket and mechanical stirrer (600 rpm), and 50 ml of catalyst solution in accordance with Example 2, corresponding to 0.32 mmol of {Mn$_2$Sb$_2$W$_{20}$}, were added. The reaction mixture was warmed to 40° C. 31.2 g of 35% strength by weight peroxide solution (0.32 mol of hydrogen peroxide) were metered in over the course of 30 minutes, and the mixture was subsequently stirred at 40° C. for a further 60 minutes. After a total time of 90 minutes, the conversion of cyclododecatriene was 37.5% with a monoepoxide selectivity of 91.0%.

EXAMPLE 18

The reaction was carried out analogously to Example 17. 20 ml of catalyst solution were used, corresponding to a starting material:catalyst molar ratio of 2500:1. After a reaction time of 120 minutes, the conversion of cyclododecatriene was 34.0%, with a monoepoxide selectivity of 92.2%.

EXAMPLE 19

The reaction was carried out analogously to Example 18, but 20 ml of catalyst from Example 3 {Sn$_2$Sb$_2$W$_{20}$} and 400 ml of toluene as solvent were used. After a reaction time of 90 minutes, the conversion was 34.2%, with a monoepoxide selectivity of 90.1%.

EXAMPLE 20

The reaction was carried out analogously to Example 17, but 50 ml of catalyst solution from Example 1 {Mn$_3$Sb$_2$W$_{18}$} and 400 ml of toluene as solvent were used. 0.32 mol of hydrogen peroxide was metered in continuously over a reaction time of 6 hours. After 6 hours, the conversion was 34.2%, with a monoepoxide selectivity of 91.7%.

EXAMPLE 21

The reaction was carried out analogously to Example 20, but o-xylene was employed instead of toluene. 50 ml of catalyst solution in accordance with Example 1, corresponding to 0.32 mmol of {Mn$_3$Sb$_2$W$_{18}$}, were employed, but methyltrioctylammonium chloride was replaced by tetrabutylphosphonium chloride in the preparation. After 6 hours, the conversion was 30.6%, with a monoepoxide selectivity of 91.8%.

EXAMPLE 22

The reaction was carried out analogously to Example 17. 50 ml of catalyst solution in accordance with Example 1, corresponding to 0.32 mmol of {Mn$_3$Sb$_2$W$_{18}$}, were employed, but methyltrioctylammonium chloride was replaced by tetrabutylphosphonium chloride in the preparation. After a reaction time of 90 minutes, the conversion was 34.5%, with a monoepoxide selectivity of 90.8%.

EXAMPLE 23
Determination of the Product Ratio

Work-up involved separation of the phases, drying of the organic phase over sodium sulfate and filtration through silica gel in order to remove the catalyst. The solvent was stripped off under reduced pressure, and the residue was subsequently separated by distillation in a high vacuum. Starting from Example 20, 33.8 g of CDT and 16.5 g of monoepoxides were obtained, together with a high-boiling residue containing diepoxides and catalyst residues. NMR analysis showed 41.6% of trans,trans-5,9-cyclododecadiene 1-epoxide and 58.4% of cis,trans-5,9-cyclododecadiene 1-epoxide. This corresponds to a cis:trans reactivity of 1.42:1.

German patent application 10055173.4, filed Nov. 8, 2001, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A method for the synthesis of a macrocyclic monoepoxide having at least one double bond, comprising:
   reacting a macrocyclic aliphatic hydrocarbon with 8 to 20 ring carbon atoms and 2 to 5 isolated double bonds, said aliphatic hydrocarbon having at least one cis double bond and at least one trans double bond, with hydrogen peroxide in two liquid phases in the presence of a catalyst system, wherein said catalyst system is a homogeneous catalyst system comprising an oxidation catalyst and a phase transfer catalyst, wherein said oxidation catalyst comprises a polyoxometallate of tungsten or molybdenum and at least one element selected from the group consisting of germanium, tin, lead, arsenic, antimony, bismuth, selenium, tellurium and polonium, and wherein said polyoxmetallate has a sandwich structure.

2. The process according to claim 1, wherein the phase-transfer catalyst comprises a cation selected from the group consisting of methyltrictylammonium, cetrimethylammonium, tetrabutylammonium, N-alkylated pyridinium and quaternary phosphonium.

3. The process according to claim 1, wherein said two liquid phases are a first phase comprising an aqueous solution of hydrogen peroxide and a second phase comprising an inert, organic water-immiscible solvent.

4. The process according to claim 1, wherein a cis double bond in said aliphatic hydrocarbon is epoxidized.

5. The process according to claim 1, wherein the polyoxometallate additionally comprises at least one transition metal from groups 4 to 12 of the Periodic Table.

6. The process according to claim 5, wherein the transition metal is selected from the group consisting of titanium, vanadium, chromium, manganese, iron, cobalt, nickel, palladium, copper and zinc.

7. The process according to claim 1, wherein said polyoxometallate anion has a structure of the formula selected from the group consisting of:

$$[(M_2(AO_2)_2(XA_9O_{33})_2 \cdot y\, H_2O]^{n-},$$

$$[M_3(XA_9O_{33})_2 \cdot y\, H_2O]^{n-},$$

$$[M_4(XA_9O_{34})_2 \cdot y\, H_2O]^{n-}, \text{ or}$$

$$[M_2X(OH)_{3-z}(AO_3)_3(XA_9O_{33})]^{n-};$$

wherein
the letters A, M and X represent the following elements:
M is Ti, V, Cr, Mn, Fe, Co, Ni, Pd, Cu, Zn, Sn or As;
A is Mo or
X is Ge, Sn, Pb, As, Sb, Bi, Se, Te or Po;
n is a number from 6 to 12;
y is a number from 0 to 6; and
z is a number from 0 to 3.

8. The process according to claim 1, wherein the phase-transfer catalyst comprises a cation selected from the group consisting of a quaternary ammonium cation, a pyridinium cation and a phosphonium cation.

9. The process according to claim 1, wherein the hydrogen peroxide is contained in a 0.1 to 85% by volume aqueous solution.

10. The process according to claim 3, wherein said solvent comprises a halogen-containing solvent selected from the group consisting of dichloromethane, 1,2-dichloroethane, chloroform, tetrachloromethane and a mixture thereof.

11. The process according to claim 3, wherein said solvent comprises a halogen-free solvent selected from the group consisting of an alkane, a cycloalkane, benzene, toluene, a xylene and a mixture thereof.

12. The process according to claim 1, wherein said reacting is carried out at a temperature of from 0° C. to 120° C.

13. The process according to claim 1, wherein said reacting is carried out at a temperature of from 5° C. to 80° C.

14. The process according to claim 1, wherein said reacting is carried out at atmospheric pressure or at a pressure which arises from the vapor pressures of the solvents.

15. The process according to claim 1, wherein said aliphatic hydrocarbon is cis,trans,trans-1,5,9-cyclododecatriene.

16. The process according to claim 1, wherein the conversion of said aliphatic hydrocarbon is at least 25%.

17. The process according to claim 1, wherein a monoepoxide selective is greater than 90%.

18. The process according to claim 15, herein a proportion of trans,trans-5,9-cyclododecadiene 1-epoxide relative to cis,trans-5,9-cyclododecadiene 1-epoxide in a product mixture is at least 35 mol %.

* * * * *